(12) United States Patent
Lim

(10) Patent No.: US 9,782,438 B2
(45) Date of Patent: Oct. 10, 2017

(54) METHOD OF PROMOTING HAIR GROWTH BY ADMINISTRATION OF BFGF

(71) Applicant: Jaehyun Lim, Seoul (KR)

(72) Inventor: Jaehyun Lim, Seoul (KR)

(73) Assignee: H CELL, INC., Austin, TX (US)

(*) Notice: Subject to any disclaimer, the term of this patent is extended or adjusted under 35 U.S.C. 154(b) by 0 days.

(21) Appl. No.: 14/802,142

(22) Filed: Jul. 17, 2015

(65) Prior Publication Data

US 2016/0279167 A1    Sep. 29, 2016

Related U.S. Application Data

(62) Division of application No. 14/665,740, filed on Mar. 23, 2015, now Pat. No. 9,173,921.

(51) Int. Cl.

| | |
|---|---|
| *C12N 5/00* | (2006.01) |
| *C12N 5/04* | (2006.01) |
| *A61K 38/18* | (2006.01) |
| *C07K 14/50* | (2006.01) |
| *A61K 35/16* | (2015.01) |
| *A61K 9/00* | (2006.01) |
| *A61K 35/19* | (2015.01) |
| *A61Q 7/00* | (2006.01) |
| *A61K 8/64* | (2006.01) |
| *A61K 8/98* | (2006.01) |

(52) U.S. Cl.
CPC ............... *A61K 35/16* (2013.01); *A61K 8/64* (2013.01); *A61K 8/983* (2013.01); *A61K 9/0019* (2013.01); *A61K 35/19* (2013.01); *A61K 38/1825* (2013.01); *A61Q 7/00* (2013.01); *C07K 14/50* (2013.01); *A61K 2800/91* (2013.01)

(58) Field of Classification Search
None
See application file for complete search history.

(56) References Cited

U.S. PATENT DOCUMENTS

| | | | |
|---|---|---|---|
| 8,518,878 | B2 | 8/2013 | Ono |
| 2003/0104079 | A1 | 6/2003 | Sakanaka et al. |
| 2003/0147831 | A1 | 8/2003 | Marko |
| 2006/0246024 | A1 | 11/2006 | Kim et al. |
| 2007/0224150 | A1 | 9/2007 | Chung |
| 2008/0286329 | A1* | 11/2008 | Campbell ........... A61L 27/3604 424/423 |
| 2010/0172865 | A1 | 7/2010 | Shantha et al. |

(Continued)

OTHER PUBLICATIONS

Lucarelli et al. European Cells and Materials vol. 20 2010, pp. 13 to 23.*

(Continued)

*Primary Examiner* — Chris R Tate
*Assistant Examiner* — Douglas F White
(74) *Attorney, Agent, or Firm* — Sughrue Mion, PLLC

(57) ABSTRACT

Disclosed are a method of promoting hair growth or preventing hair loss in a mammal. In one aspect, the method includes administering interdermally or subcutaneously an agent containing an active ingredient comprising bFGF and a pharmaceutically acceptable substance, wherein bFGF is administered in a dose of 1 μg to 100 μg per 1 cm$^2$ of the target area of hair growth treatment or hair loss prevention and a composition for use in the method.

**11 Claims, 9 Drawing Sheets
(8 of 9 Drawing Sheet(s) Filed in Color)**

(56) References Cited

U.S. PATENT DOCUMENTS

| | | |
|---|---|---|
| 2011/0217260 A1 | 9/2011 | Shantha et al. |
| 2012/0171161 A1 | 7/2012 | Abramson et al. |
| 2012/0171180 A1 | 7/2012 | Abramson et al. |
| 2012/0322882 A1 | 12/2012 | Trogden et al. |
| 2014/0079686 A1 | 3/2014 | Barman et al. |
| 2014/0335046 A1 | 11/2014 | Matheny |
| 2015/0071877 A1 | 3/2015 | Maguire et al. |

OTHER PUBLICATIONS

Emin Tuncay Ustuner, "Cause of Androgenic Alopecia: Crux of the Matter," Plastic Reconstructive Surgery Global Open, International Open Access Journal of the American Society of Plastic Surgeons, Oct. 28, 2013, pp. 1-5.

Mototsugu Fukaya et al., "A New Economic Method for Preparing Platelet-rich Plasma," Plastic Reconstructive Surgery Global Open, International Open Access Journal of the American Society of Plastic Surgeons, Jun. 3, 2014, pp. 1-7.

Ozeki, et al., "Promoted Growth of Murine Hair Follicles through Controlled Release of Basic Fibroblast Growth Factor," Tissue Engineering 8(3):359-366 (2002).

du Cros, "Fibroblast Growth Factor and Epidermal Growth Factor in Hair Development," Journal of Investigative Dermatology 101:106S-113S (1993).

Jimenez, et al., "Protection from 1-?-D-Arabinofuranosylcytosine-induced Alopecia by Epidermal Growth Factor and Fibroblast Growth Factor in the Rat Model," Cancer Research 52:413-415 (Jan. 15, 1992).

Dhurat, et al., "A Randomized Evaluator Blinded Study of Effect of Microneedling in Androgenetic Alopecia: A Pilot Study," International Journal of Trichology, 5(1):6-11 (Jan.-Mar. 2013).

* cited by examiner

Fig. 3B

METHOD OF PROMOTING HAIR GROWTH BY ADMINISTRATION OF BFGF

CROSS-REFERENCE TO RELATED APPLICATIONS

This application is a divisional of U.S. application Ser. No. 14/665,470 filed Mar. 23, 2015 (allowed), the disclosure of which is incorporated herein by reference in its entirety.

BACKGROUND OF THE DISCLOSURE

I. Field of the Disclosure

A non-limiting embodiment relates to a method of promoting hair growth or preventing hair loss, comprising administering intradermally or subcutaneously Basic fibroblast growth factor (bFGF) or a mixture of bFGF with platelet rich plasma (PRP) and/or blood plasma.

II. Description of the Related Art

Hair loss can cause someone to look notably older than his or her actual age and can otherwise make him or her look less attractive. The cause of hair loss includes a part of the natural aging process, compromised hair growth cycle, genetic predisposition, unwanted side effects from medication and/or medical treatment, environmental causes such as allergies, infections, stress, a lack of proper diet and sleep, and/or other systematic disorders.

According to research results available in the web (e.g., www.statisticbrain.com/hair-loss-statistics), by age 35, it is estimated that 40% of males in the United States will have some noticeable hair loss. This condition gets worse as men get older. By age 60, it is estimated that 65% of adult males in the United States will suffer from noticeable hair loss. FIG. 1 shows that male-pattern baldness occurs in varying forms with a significant portion of the male population.

Women also suffer from hair loss. Female hair loss, unlike in men, typically involves noticeable thinning all over the head and the hairline. The American Academy of Dermatology reports that 40% of women have noticeable hair loss by the age 40. Despite this widespread problem, hair loss may not be seen as normal or acceptable for women due in part to social norms that may pressure women to look their best. Even a slight thinning of hair, if noticeable, may be undesirable to a woman's self-image and how others may judge her.

Therefore, many attempts to prevent and treat hair loss including medications, invasive surgical procedures, and injections have been made in the market. Medications such as MINOXIDIL® (Rogains), FINASTERIDE® (Propecia) and DUTASTERIDE® (Avodart) are an approved treatment for hair loss. However, these medications have shortcomings because, to be effective, the patient is required to take the medication daily. Further, the medication will work in the long term only if the patient continues to take the medication. Any discontinuance is likely to result in the loss of any hair gained. Moreover, some of these medications are not approved for use by women because of safety concerns.

Invasive hair loss treatment available includes surgical procedures such as follicle unit transplantation, scalp reduction or scalp flaps, and injection methods. These surgical procedures have a risk of possible skin necrosis or keloid scar tissue formation at donor region. These surgical procedures also often produce unsatisfactory results such as unnatural looking hair growth due to direction of hair growth and limitations on the number of hair follicles that can be safely transferred (less than 4000 hair follicles can be transferred every procedure with the maximum of 3 procedures in a patient's entire life). Such surgical treatment is also inconvenient for patients because it often requires 3-4 hours of operation, post-operative care, and disruption of normal daily living immediately after the surgery for approximately 2 weeks (even without complications).

Currently, there are also many different types of injection methods, such as methotherapy, plate rich plasma (PRP)-alone injection, PRP+ACELL® Injection, and others. A wealth of literature has already considered the use of PRP in sports medicine, orthopedic surgery, dental surgery, and a number of other medical and surgical specialties to enhance tissue repair and healing after surgical procedures or injury. Every platelet is a biochemical storehouse of regulatory, signaling and growth-factor molecules that participate in recovery and healing of tissue as well as emergency response to injury. Growth-factor molecules associated with platelets include: Platelet-derived growth factor (PDGF), Transforming growth-factor-beta (TGF-b), Vascular endothelial growth factor (VEGF), Epidermal growth factor (EGF), Fibroblast growth factor-2 (FGF-2), and Insulin-like growth factor (IGF) (International Society of Hair Restoration Surgery, Platelet-Rich Plasma in Hair Transplantation, Oct. 1, 2009).

Based on this literature, PRP injections and PRP+ACELL® Injection have been used for treating hair loss. However, the results of these injection methods vary widely. Often the results are conflicting and questionable. The existing injection method treatment, while restoring hair to some individuals, lacks the consistency to make it work for significant other populations suffering from hair loss.

Having perceived such lack of effective treatment for hair loss, the inventor looked at leading theories on hair loss, including (a) Dihydrotestosterone Theory, (b) Gravity Theory, and (c) Blood Supply Theory.

Dihydrotestosterone Theory is currently the leading theory hypothesizing that dihydrotestosterone (DHT) binds to hair follicles and shrinks hair follicles, making it impossible for healthy hair to survive. However, this theory does not explain why high levels of DHT do not affect hair loss to some individuals. Most men with high levels of DHT still have growing hair in the back of their heads and sides. In addition, these men also have healthy growing hair in other parts of their body such as armpit, legs, chest, and pubic area.

One theory trying to answer such paradoxical result of the Dihydrotestosterone Theory is the Gravity Theory of Hair Loss ("Gravity Theory"). This theory hypothesizes that the effects of gravity may be a contributing factor to hair loss. One special-topic paper in Plastic and Reconstruction Surgery reports that androgenic effect makes the thinning of the scalp. This thinning causes the scalp to have less ability to hold hair's weight firmly. This in turn causes hair to be unintentionally pulled out easier and earlier than the normal end of anagen (hair growing period) phase. Gravity gradually thins the skin on a person's scalp and this thinning of the skin causes the affected area to lose the ability to hold and grow hair. Emin Tuncay Ustuner reports that the thinned skin cannot afford the weight of hair for long and therefore hair can be pulled out easily (Cause of Androgenic Alopecia, Plastic & Reconstructive Surgery Global Open 2013; 1 DOI: 10.1097/GOX.0000000000000005).

There are three phases in a person's hair cycle: Anagen, Catagen, and Talogen. Anagen is the hair growing phase in the cycle, which in a healthy person typically lasts 4 to 6 years. Catagen is the phase in the cycle marking the end of the hair growth, which in a healthy person typically lasts 2 to 3 weeks. Finally, Talogen is the dormant (resting) phase marked by no growth of hair, which in a healthy person typically lasts 3 months.

According to the Gravity Theory, the thinning of the skin in the balding area of the head causes substantial shortening of Anagen phase (growth phase). The thinning of the skin also lengthens the Talogen phase.

Another theory, called Blood Supply Theory, argues that the cause of baldness is that a lack of blood supply to the follicles substantially shortens anagen phase (hair growth period) and prolongs talogen phase (resting—no hair growth phase). This theory is backed up by a product called MINOXIDIL® which was originally marketed as medication to treat high blood pressure based for its vasodilatation property on hypertension. It was discovered that one of MINOXIDIL®'s side effects was hair growth in bald and thinning areas. Because MINOXIDIL® enhances blood supply with its vasodilatation function, it is currently being used to treat hair loss. While the patient is administered MINOXIDIL®, blood supply to the follicles is increased and hair growth is temporarily stimulated.

Regardless of the theories explaining the causes of thinking hair or hair loss, there is not a treatment which provides satisfactory results of hair regain or hair growth promotion.

The present disclosure is directed to stimulating hair growth. An exemplary embodiment of stimulating hair growth shows that it thickens the skin in the target area by triggering fibrogenesis and tissue regeneration as well as increases the blood supply in the target area by making new blood vessels in the area.

SUMMARY OF THE DISCLOSURE

Surprisingly, the inventor has found, based on clinical research, that bFGF or a mixture of bFGF with PRP and/or Plasma is effective to stimulate hair growth when administered intradermally or subcutaneously to the scalp of patients. Based on this finding, it is determined that bFGF, a mixture of bFGF and PRP, a mixture of bFGF and Plasma, and a mixture of bFGF, PRP, and blood plasma (hereinafter, sometimes together referred to as "Agent") are all effective to stimulate hair growth. Based on this finding, it is also determined that the Agent will be effective in growing hair in other areas, such as eyelashes, eyebrows, mustache, beard region, and other areas of the skin of a patient. The inventor has further found, based on clinical research, that the Agent is effective to stimulate hair growth in both women and men of the age of 18 or older, at any scale and type of the hair loss.

The inventor found that when administering intradermally or subcutaneously bFGF or its mixture with PRP and/or plasma, rather than using it for external application on the skin surface, bFGF or the bFGF mixture surprisingly exerts significant advantageous effects on hair growth. bFGF in combination with PRP and/or plasma may be used in an amount effective to attain the desired results, such as increase hair number, thicker hair, increased hair growth, decrease of hair loss and the like.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Objects and advantages of illustrative, non-limiting embodiments will become more apparent by describing them in detail with reference to the attached drawings in which:

FIG. 3A shows an illustrative embodiment of a target area before the treatment in accordance with the disclosure in Case 1;

FIG. 3B shows an illustrative embodiment of a target area 4 months after the treatment in accordance with the disclosure in Case 1;

DETAILED DESCRIPTION OF ILLUSTRATIVE, NON-LIMITING EMBODIMENTS

Figure 1:
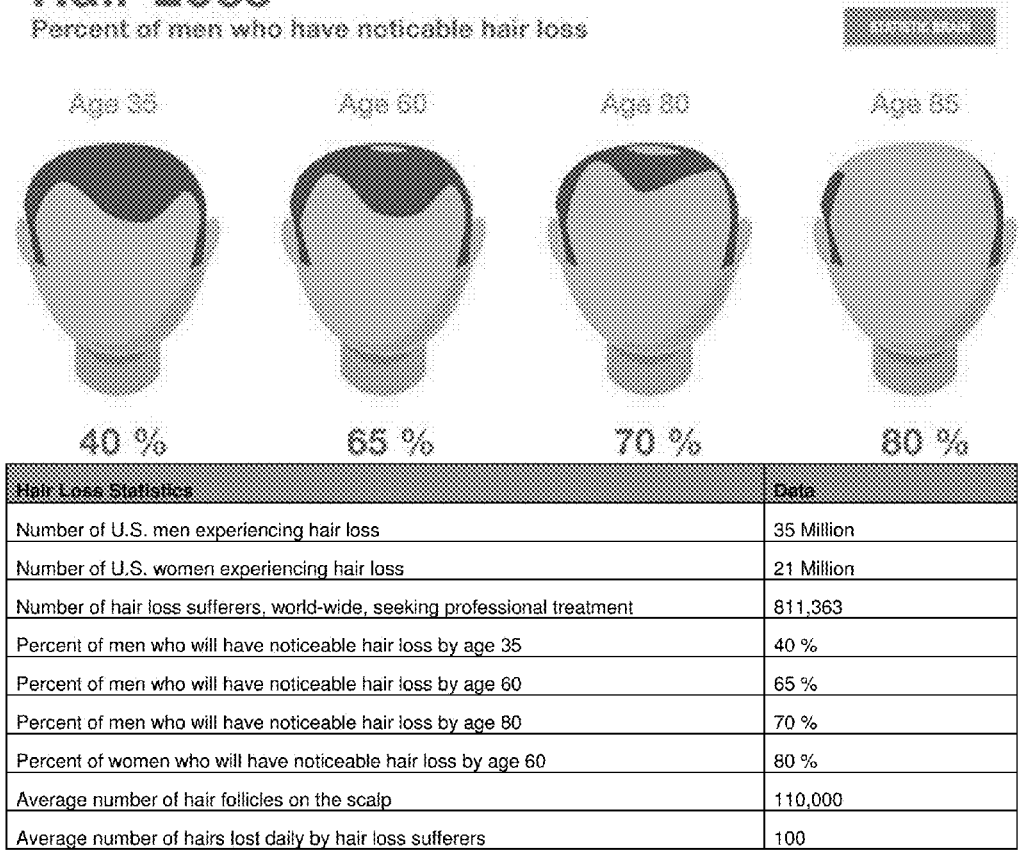
FIG. 1 shows that male-pattern baldness occurs in varying forms with a significant portion of the male population.

The following description of the illustrative, non-limiting embodiments discloses specific processes and ingredients. However, the embodiments are merely examples, and thus, the specific features described below are merely used to more easily describe such embodiments and to provide an overall understanding. Accordingly, one skilled in the art will readily recognize that the disclosure is not limited to the specific embodiments described below. Furthermore, the descriptions of various processes and ingredients of the embodiments that would have been known to one skilled in the art are omitted for the sake of clarity and brevity.

According to exemplary embodiments, bFGF or its mixture with PRP and/or plasma may be administered in an effective amount intradermally or subcutaneously to attain the desired advantageous effects of promoting hair growth.

bFGF, optionally in combination with plasma (in an embodiment, in gel-type plasma) and/or PRP may administered intradermally or subcutaneously, either prior to or after a sterilized micro-needle therapy system (MTS), which more effectively stimulates skin regeneration in the treated areas. This is done by causing a slight controlled skin injury at a tolerable rate and stimulating repair of that area. The MTS causes a slight controlled injury to the epidermis of the target area when the epidermis is penetrated repeatedly by micro-needles which trigger stimulation of collagen and elastin. The injected mixture of plasma, PRP, and bFGF solution helps with the skin repair and regeneration of the target area. Plasma, PRP, and bFGF have fibroblast generating properties. Therefore, this process promotes thickening of the skin in the treated area.

Both PRP and bFGF are reported to have angiogenesis-inducing activity in vitro and in vivo. Both PRP and bFGF are used to heal wounds. By mixing PRP and bFGF, our research has shown that a more potent blood vessel formation can occur. Using the MTS causes a slight controlled injury to the epidermis of the target area when the epidermis is penetrated repeatedly by micro-needles. The injected mixture of plasma and PRP helps to repair this injury while helping to form new blood vessels in the target area. The new blood vessels help to supply more blood in the target area.

The agent according to the procedure for promoting hair growth is not particularly limited, as long as it contains bFGF, a mixture of bFGF and Plasma, a mixture of bFGF and PRP, or a mixture of bFGF, Plasma, and PRP and is administered intradermally or subcutaneously with various injection tools. Hair growth includes, without limitation, stimulating the conversion of telogen phase of hair cycle to anagen phase in order to normalize (or at least improve interrupted) hair cycle and normalize shortened anagen phase, resulting in regaining hair, improve hair health, thickening hair in the treated area.

The effective amount of plasma, PRP, and bFGF or the dosage thereof is not particularly limited, and generally, it can be administered in an amount of 0.1 μg to 1 mg of bFGF per $cm^2$ of skin surface that is the target of hair growth treatment. In an exemplary embodiment, bFGF may be used in an amount of 1 μg to 100 μg, or 0.1 μg to 50 μg, or 10 μg to 100 μg of bFGF per 1 $cm^2$ of skin surface that is the target of hair growth treatment.

Plasma may be used in an amount of 0.05 ml to 40 ml per $cm^2$ of skin surface. In an exemplary embodiment, plasma may be used in an amount of 0.05 ml to 20 ml, 0.05 ml to 15 ml, or 10 ml to 30 ml per $cm^2$ of skin surface.

PRP may be obtained directly from whole blood of a patient to be treated or a commercially available product could be used. PRP contains an increased number of plates, compared to a naturally occurring plasma. For example, PRP, which can be used in the exemplary embodiments, may contain at least twice, at least three times, at least four times, at least five times, at least six times, at least seven times, at least eight times, at least nine times, at least ten times, at least eleven times or at least twelve times greater than the normal platelet counts in human blood. RPR may be used in an amount of 0.01 ml to 20 ml per $cm^2$ of skin surface. In an exemplary embodiment, PRP may be used in an amount of 0.01 ml to 15 ml, 0.01 ml to 10 ml, or 5 ml to 20 ml per $cm^2$ of skin surface. An agent according to an embodiment may include (a) bFGF in an amount of effective to promote hair growth; and (b-1) platelet rich plasma (PRP), (b-2) blood plasma, or (b-3) a mixture of PRP and blood plasma. Amounts of PRP and plasma in the agent are 0.1-10 times and 0.2-20 times by volume, respectively, based on 1 ml of bFGF solution, said 1 ml of bFGF solution containing 100 μg of bFGF.

In an embodiment, the composition may consists essentially of (a) bFGF in an amount of effective to promote hair growth; and
(b-1) platelet rich plasma (PRP),
(b-2) blood plasma, or
(b-3) a mixture of PRP and blood plasma.

In another embodiment, the composition may consists of (a) bFGF in an amount of effective to promote hair growth; and
(b-1) platelet rich plasma (PRP),
(b-2) blood plasma, or
(b-3) a mixture of PRP and blood plasma.

These compounds may be administered sequentially or as a mixture. For example, in an exemplary embodiment, combination may occur just before administering the Agent to the scalp of the patent.

Further, the frequency of administration is not particularly limited, and it can exert a sufficient effect by a single administration. From the viewpoint of sustaining superior effects, it is preferred to administer the mixture periodically for a certain period of time, for example, once a month for 3 months. It is recommended that the frequency be varied based on the health and condition of the patient's hair and the results desired by the patient.

bFGF is currently available in the market for only topical application or topical spraying. For example, bFGF which is marketed under TRAFERMIN™ (KAKEN PHARMACEUTICAL CO., LTD) can be used. However, other commercially available bFGFs could be used to obtain similar results. bFGF can be used as they are currently available or diluted or dispersed in a solvent, mixed with a suspending agent, or emulsifying agent, which will be explained in more detail hereinafter.

PRP and plasma may be obtained from the patient who is subject to the treatment. For example, a proper amount of whole blood may be drawn from the patient on the day of the treatment and the whole blood is centrifuged to separate plasma and PRP. The separation could be conducted by following known techniques. The collected whole blood or separated blood (i.e., PRP and plasma) may be stored under proper conditions until they are used in the treatment. The proper amount of the whole blood may be determined depending on the general condition of the patient's health and the condition of targeted area. The source of the whole blood is not limited to the patient to be treated. The whole blood could be drawn one day or more prior to the treatment and can be stored under appropriate conditions. As will be explained in more detail below, plasma may be used as a gel-like form.

The following explanation of a non-limiting, illustrative embodiment of a treatment procedure for promoting hair growth involves 9 steps. However, one or more of the steps may be omitted and/or carried out in a different sequence, as long as the agent which contains bFGF, optionally in combination with PRP and plasma are intradermally or subcutaneously administered to a patient.

Step 1: Collect Various Amounts of Blood from Patient

On the date of the treatment, whole blood is drawn from a patient who is being treated, using a conventional method of drawing blood. The volume of the blood drawn depends on the overall health and hair loss state of the patient being treated. All the blood drawn is utilized for that patient's procedure that day. There should not be any extra blood drawn more than necessary for the treatment.

Step 2: Separate Obtained Blood

Plasma, PRP (platelet rich plasma), and RBC (Red Blood cell) from the blood drawn from Step 1 are separated by a centrifuge-utilizing equipment. The centrifugation separates the platelet-rich plasma from platelet-poor plasma and red blood cells because of differences in specific gravity. There are, at present, two methods of PRP preparation approved by the U.S. Food and Drug Administration (FDA). Both processes involve the collection of a patient's whole blood (that is anticoagulated with citrate dextrose) before undergoing two stages of centrifugation (TruPRP) (Harvest) designed to separate the PRP aliquot from platelet-poor plasma and red blood cells. In humans, a typical baseline blood platelet count is approximately 200,000 per μL; therapeutic PRP concentrates the platelets by roughly four-fold. There is, however, broad variability in the production of PRP by various concentrating equipment and techniques. Most of commercially available kits adopt anticoagulant dextrose solution A ("ACD-A") as an anticoagulant even though there are others such as heparin or EDTA (ethylenediaminetetraacetic acid). Moreover, no kits take the platelet aggregation inhibitor into consideration, although coagulation and platelet aggregation are very different and anticoagulants never suppress platelet aggregation (Plastic and Reconstructive Surgery—Global Open: June 2014, vol. 2, issue 6, p e162 doi: 10.1097/GOX.0000000000000109).

Step 3: Soak Sterilized Polypropylene Container Containing Plasma in Safe and Effective Temperature for Specified Time to Make Gel-Type Plasma Separated Plasma in a sterilized container is submerged in boiled water at the optimal temperature (0° C. to 100° C.) for optimal time (0 minutes to 10 minutes) to create gelatinous form called "Gel-Type Plasma." The Gel-Type Plasma obtained from this step will be mixed with bFGF solution obtained from Step 4 below in a safe and effective amount between Plasma and bFGF. This prepared solution is again mixed with some portion of a prepared mixture of PRP and bFGF (from Step 5(b)). Gelatinous form (or semi-solid form) has better retention when the solution is injected onto the target skin area, but the plain mixture of plasma (not having been submerged in the optimal temperature for specific time) and bFGF can also be used. The quantity and proportion between bFGF and Plasma can vary depending on the condition of hair loss. This solution will serve as thickening targeted skin and scalp.

Step 4: Prepare bFGF Solution

500 μg of the freeze-dried commercially purchased bFGF is dissolved into 5 ml of saline solution to prepare 100 μg/ml of bFGF solution. The dissolution of bFGF occurs instantly to create the bFGF solution. The bFGF solution is prepared such that it is in an injectable form. The bFGF solution is stored in refrigeration, below 10° C. until ready for use on the day or up to two weeks later for future use.

Step 5: Prepare the Following Two Compounds (a) Mix the following to obtain the PRP+bFGF solution:
 (1) PRP (0.5 ml to 20 ml) obtained from Step 2, and
 (2) bFGF solution (0.1 μg to 10 mg) obtained from Step 4.

(b) Mix the following to obtain the Plasma+bFGF+PRP solution:
 (1) Plasma (1 ml to 40 ml) obtained from Steps 2,
 (2) bFGF solution (0.1 μg to 10 mg) obtained from Step 4, and
 (3) PRP+bFGF solution obtained from Step 5(a).

Separated PRP and bFGF are mixed in a safe and effective amount between PRP and bFGF to create injectable solution, which will serve as promoting or stimulating hair growth. The actual volume of the items listed above depends on the overall health and hair loss state of the patient being treated. In this exemplary example, bFGF, PRP and Plasma are mixed at a ratio of approximately 1:1.09:2.36 (bFGF:PRP:Plasma). There is no specific order of mixing or administering the compound. For convenience, when bFGF is administered in combination with PRP and/or plasma, these compounds could be administered as a mixture, rather than administered singly. In an exemplary embodiment, a mixture of RPR and bFGF, a mixture of bFGF and plasma, or a mixture of bFGF, PRP, and plasma may be administered. When administered singly, there is no limitation of administering individual compounds. When a multiple treatment is carried out for one patient, each treatment may comprise an identical compound/combination, or different compounds/combinations, which can be determined by a doctor who provides the treatment depending on the outcome of the first/previous treatment. For example, in exemplary embodiment, a mixture of PRP and bFGF, and a mixture of plasma, bFGF, and PRP may be administered in this order for a first and a second treatment, respectively. Still in another exemplary embodiment, different agents, for example, a mixture of gel-type plasma+PRP+bFGF solution and a mixture of PRP+bFGF solution may be administered sequentially in this order during a single treatment.

Step 6: Administer Anesthetic Procedure on the Patient

Depending on the patient's condition and preference, different methods of anesthetics can be used, such as local anesthesia, nerve block, or general anesthesia.

Step 7: Preparation of Target Area with Micro-Needle Therapy System (MTS)

Sterilized micro-needle therapy system (MTS) stimulates skin regeneration in the treated areas. This is done by causing a slight controlled skin injury at a tolerable rate and stimulating repair of that area. The MTS promotes absorption of prepared mixtures and triggers the inflammation process. The MTS causes a slight controlled injury to the epidermis of the target area when the epidermis is penetrated repeatedly by micro-needles which trigger stimulation of collagen and elastin.

Step 8: Inject the Target Area(s)

Inject the target area with the following compounds in the following preferable sequence:
 (a) Gel-Type Plasma+PRP+bFGF solution [obtained from Step 5(a)]
 (b) PRP+bFGF solution [obtained from Step 5(b)]

The two injections are administered in sequence intradermally or subcutaneously onto the target site(s) by various injection tools in a safe and effective amount, for example, 0.1 μg to 50 μg or 1 μg to 100 μg of bFGF per $cm^2$ of treatment area, not exceeding 1000 μg of bFGF administration a day. The amount can vary depending on the condition of hair loss and the patient's overall health. The listed sequence of administering the two injections is thought to be preferable.

This step is relatively convenient because it requires approximately 20-180 minutes of injection administration time, which allows patients to immediately return to normal daily living the following day, including taking showers.

Step 9: Repeat the Entire Process

Preferably, the procedure described herein is repeated at least once a month (but no more than once a week), more preferably on a monthly basis for at least 3 months, and most preferably for longer period of time, for example, for about 1 year. Frequency of injection can be varied and multiple procedures can be done.

Use of bFGF in treating skin aging and wrinkle skin is known in the art, for example in U.S. Pat. No. 8,518,878 and various causes and symptoms of hair loss or hair thinning are known in the art, for example in US Patent Application Publication No. 2012/0322882, which are incorporated in their entities by reference herein, where appropriate.

The agent of the present disclosure may be used for treating various hair loss disorders including, but not limited to, alopecia greata, telogen effluvium, anagen effluvium, cicatricial, alopecia, scarring alopecia, scalp thinning; hair shaft abnormalities such as trichorrexis nodosa, loose anagen syndrome, trichotillomania, and traction alopecia; infectious hair disorders such as tiniea capitis, sebohorreic dermatitis, and follicullitus of the scalp; genetic disorders such as androgenic alopecia, and patients undergoing hair loss due to chemotherapy, radiation therapy, hormonal imbalance (e.g., thyroid conditions such as hypothyroidism and hyperthyroidism, pregnancy, child birth, discontinuation of birth control pills and changes in menstrual cycle), fungal infection of the scalp such as ringworm, medicines causing hair loss such as anti-coagulants, medicine for gout, depression, high blood pressure, and certain heart medications. The agent may also be used to treat hair loss related to environmental factors and chemicals used in hair treatment (dying, tinting and bleaching).

The agent of the present disclosure may be used to treat hair loss related to other diseases such as diabetes, lupus, and poor nutrition, mental/physical stress such as due to surgery, illness, and high fever.

Preferably, the agent of the present disclosure is administered to a target area of the body multiple times at a certain interval of, for example 2-6 weeks, or 3-5 weeks. In an aspect, the agent may be administered at least once a month (but no more than once a week), more preferably on a monthly basis for at least 3 months, and most preferably for longer period of time, for example, for about 1 year.

The agent of the present disclosure may comprise a pharmaceutically acceptable carrier. bFGF used in the present disclosure may be formulated into an appropriate formulation following a common method. The formulation may be a solid formulation such as powder and granule. However, from the viewpoint of obtaining a superior efficiency for preventing and treating hair loss, it may be preferably formulated into a liquid agent for injection such as a solution agent, emulsion, suspension agent, or into a gelling agent for injection. As a method for producing the liquid agent, for example, a method comprising mixing bFGF with a solvent, and a method comprising further mixing bFGF with a suspending agent, or emulsifying agent can be preferably exemplified. As a method for producing the gelling agent, for example, a method of mixing bFGF with gelatin can be preferably exemplified. When formulating bFGF of the present disclosure into a formulation, an appropriate pharmaceutically acceptable carrier, e.g., any component such as excipient, binding agent, solvent, solubilizing agent, suspending agent, emulsifying agent, tonicity agent, buffering agent, stabilizing agent, soothing agent, antiseptic agent, antioxidant agent, coloring agent, may be compounded to suit the needs in formulation.

Examples of the solvents include hydrophilic solvent such as purified water, physiological saline, Ringer's solution, ethanol, propylene glycol, glycerin, polyethylene glycol, macrogol, etc.; and lipophilic solvent such as olive oil, peanut oil, sesame oil, camellia oil, canola oil, fatty acid monoglyceride, fatty acid diglyceride, higher fatty acid ester, liquid paraffin, etc. Examples of the above suspending agent include stearyl triethanol amine, sodium lauryl sulfate, lauryl aminopropionate, lecitin, benzalkonium chloride, benzethonium chloride, glyceryl monostearate, polyvinyl alcohol, polyvinylpyrrolidone, sodium carboxymethyl cellulose, methyl cellulose, hydroxymethyl cellulose, hydroxyethyl cellulose, hydroxypropyl cellulose, polysolvates, polyoxy ethylene hydrogenated castor oil, gum arabic, bentonite, etc. Further, examples of the above emulsifying agent include gum arabic, gelatin, lecithin, cholesterol, yolk, bentonite, Veegum, cetanol, glyceryl monostearate, methyl cellulose, sodium carboxymethyl cellulose, stearic acid, etc.

Examples of the above solubilizing agent include polyethylene glycol, propylene glycol, D-mannitol, trehalose, benzyl benzoate, ethanol, trisaminomethane, cholesterol, triethano lamine, sodium carbonate, sodium citrate, sodium salicylate, sodium acetate, etc. Examples of the above excipient include lactose, white soft sugar, D-sorbitol, starch, pregelatinized starch, corn starch, D-mannnitol, dextrin, crystalline cellulose, gum arabic, low-substituted hydroxypropyl cellulose, sodium carboxymethyl cellulose, methyl cellulose, serum albumin, etc. Examples of the above binding agent include pregelatinized starch, sucrose, gelatin, gum arabic, methyl cellulose, carboxymethyl cellulose, sodium carboxymethyl cellulose, crystalline cellulose, white soft sugar, D-mannitol, trehalose, dextrin, pullulan, hydroxypropyl cellulose, hydroxypropyl methyl cellulose, polyvinyl pyrrolidone, polyvinyl alcohol, etc.

Examples of the above tonicity agent include sodium chloride, potassium chloride, glucose, fructose, mannitol, sorbitol, lactose, saccharose, glycerin, urea, etc. Further, examples of the above buffering agent include sodium citrate, glycerin, etc. Examples of the above antiseptic agent include paraoxy benzoic acid esters, chlorobutanol, benzyl alcohol, phenethyl alcohol, dehydroacetic acid, sorbic acid, etc. Examples of the above stabilizing agent include polyethylene glycol, dextran sulfate sodium, amino acid, human serum albumin, etc. Examples of the above soothing agent include glucose sugar, calcium gluconate, procaine hydrochloride, etc. Furthermore, examples of the above antioxidant agent include sulfite, ascorbic acid, vitamin D, etc. Examples of the above coloring agent include tar pigment, caramel, colcothar, titanium dioxide, FD & C pigments such as FD & C blue No. 2, and FD & C red No. 40 from Ellis & Everard, etc.

Further, the agent for stimulating hair growth and treating hair loss can contain, besides bFGF, a substance having or expected to have an effect on preventing and treating hair loss. Examples of substances having or expected to have the above effect preferably include one or more selected from the group consisting of morphogens such as fibroblast growth factor 10 (FGF10), acidic fibroblast growth factor (FGF1), vascular endothelial growth factor (VGEF), insulin-like growth factor (ILGF), hepatocyte growth factor (HGF), epidermal growth factor (EGF), etc. By administering those substances intradermally or subcutaneously in addition to the agent for preventing and treating hair loss, they may be used in combination with the agent for preventing and treating hair loss.

The method of administering the agent for preventing and treating hair loss of the present disclosure intradermally or subcutaneously is not particularly limited as long as it is a method for administering the agent intradermally or subcutaneously to the site of hair loss, or surrounding part thereof, being the target of prevention or treatment.

As used herein, the following terms are defined as follows.

"Basic Fibroblast Growth Factor" and "bFGF" is a biopharmaceutical product that is widely available in commercial markets and used for treating many skin disorders and used as wound healing agent, e.g., bFGF commercial product " Trafermin" from Daewoong Pharmaceutical, Co., Ltd, the Republic of Korea, one of the distributor of Kaken Pharmaceutical, Co., LTD., etc. As long as it has an effect on preventing and treating hair loss of the present disclosure, the aspect of bFGF may be any of a naturally occurring type- or genetically modified type-bFGF, or a precursor protein thereof; a protein wherein one or more constituent amino acids of the naturally occurring type- or genetically modified type-bFGF have been substituted, deleted, or inserted; a protein encoded by a cDNA that can hybridize under stringent conditions (65° C., 1×SSC, 0.1% SDS or 0.1×SSC, 0.1% SDS) to a naturally occurring type-human bFGF; a protein having a homology of 75% or more, preferably 80% or more, more preferably 85% or more, further preferably 90% or more, and further more preferably 95% or more to the naturally occurring type-human bFGF cDNA. Further, it may be a nucleic acid encoding a gene of each protein (cDNA or cDNA plasmid; hereinafter sometimes referred to as "gene" as a whole). The genes can be administered as a single plasmid, or in a form of a complex plasmid in which liposome, etc. are combined with an expression vector.

"Plasma" means the top liquid portion of blood, when centrifuged, obtained from blood withdraw from the patient who wishes to prevent and treat his/her own hair loss—a protein-salt solution in which red and white blood cells and platelets are suspended. Plasma, which is 92 percent water, constitutes 55 percent of blood volume. Plasma contains albumin (the chief protein constituent), fibrinogen (responsible, in part, for the clotting of blood), and globulins (including antibodies). Plasma serves a variety of functions, from maintaining a satisfactory blood pressure and volume to supplying critical proteins for blood clotting and immunity. It also serves as the medium for exchange of vital minerals such as sodium and potassium and helps to maintain a proper pH (acid-base) balance in the body, which is critical to cell function. Plasma is obtained by separating the liquid portion of blood from the cells.

"Platelet Rich Plasma" and "PRP" means the blood mid portion of blood when centrifuged, obtained from blood withdraw from the patient who wishes to prevent and treat his/her own hair loss, being blood plasma that has been enriched with platelets. As a concentrated source of autologous platelets, PRP contains several different growth factors and other cytokines that stimulate healing of bone and soft tissue.

"Gel-Type Plasma" means the resulting product when Plasma has been submerged in sterilized polypropylene container in safe and effective temperature for specified time to make gelatinous form for better retention when the solution is injected onto the target skin area. It may be created using Step 3 mentioned in Example below.

"bFGF Solution" means the resulting product when freeze-dried commercially purchased bFGF is dissolved into saline solution, benzalkonium chloride or similar solvent. It may be created using Step 4 mentioned in Example below.

"PRP and bFGF Solution" means the resulting product when PRP is mixed with bFGF solution. It may be created using Step 5(b) mentioned in Example below.

"Anesthetic" means local anesthesia, nerve block, or general anesthesia in the procedure that is the practice of administering medications either by injection or by inhalation (breathing-in) that block the feeling of pain and other sensations, or that produce a deep state of unconsciousness that eliminates all sensations, which allows medical and surgical procedures to be undertaken without causing undue distress or discomfort.

"Clinical research" means the treatments conducted by the inventor at a clinic in confidential manner as detailed in the Cases below, which confirmed the effect of hair growth with the Agent. "Intradermal" means administering an agent (preferably by injection) into dermal tissue of the skin.

"Subcutaneous" means administering an agent (preferably by injection) into adipose tissue under the skin.

"Hair" means scalp, head, facial and/or body hair, including but not limited to the scalp, eye lashes, brows, mustache, beard, ear, nasal, chest, pubic, auxiliary, and the like.

"Hair growth" means earlier inducing growth of a new hair cycle, prolonging the active growth phase (anagen) of the hair cycle, increasing the growth rate of the hair, and/or increasing the width of hair shaft, including, but not limited to, the induction of the growth of hair and making it more visible to the eye.

"Hair Loss" and "Hair Thinning" means a decrease in normal hair density and/or shortening of the normal growth phase (anagen) of the hair cycle and/or reduction of the width of hair shaft, and reduction of the number of hairs, which may be caused by age increase, genetically predisposed and/or other causes, and may be suffered by male or female, young or old.

The term "promote hair growth" or "treatment" used herein is intended to mean at least one of the results of an increase in number and/or length and/or thickness of hair on at least part of the treated skin (or scalp) surface.

"Prevent" and "Preventing" as used herein concerning hair loss or hair thinning means an effect on decreasing any hair loss or hair thinning in advance.

"Procedure" means a series of steps that is outlined in the Example titled "Methodology and Steps," including collecting blood and separating blood; making and using certain solutions that include bFGF, preparing the patient and target area with anesthetics and micro-needle therapy system, and intradermal and subcutaneous injection of the target area.

"Safe and Effective Amount" means an amount sufficient that the Agent can provide the hair growth stimulation effect at a reasonable benefit/risk ratio attendant with any medical treatment. Within the scope of sound medical judgment, the amount and proportion of active ingredients used can vary with the particular condition being treated, the severity of the condition, the cause of the condition, the duration of the treatment, the specific active ingredient employed, its concentration, the specific vehicle utilized, the general health of the patient, the tolerance of the patient to various effects of the administration, other drugs being administered to the patient, and like factors within the specific knowledge and expertise of the patient or attending physician.

Further, the present disclosure also encompasses the use of bFGF in the manufacture of an agent for preventing and treating hair loss; a method for using bFGF in an agent for preventing and treating hair loss; the use of bFGF in the prevention and treatment of hair loss; a method for preventing and treating hair loss comprising administering intradermally or subcutaneously bFGF to mammals (particularly human); a method of making a mixture of bFGF with other substances, such as PRP and/or Plasma for such purpose.

EXAMPLE

Figure 2A:
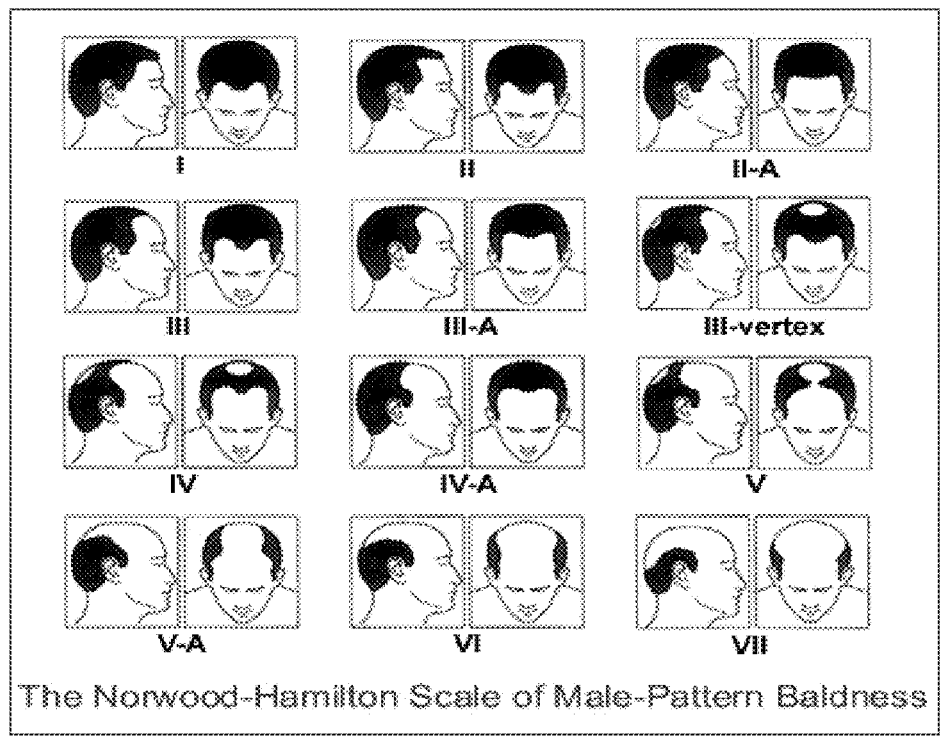
FIG. 2A shows Norwood-Hamilton scale of male-pattern boldness.
Figure 2B:
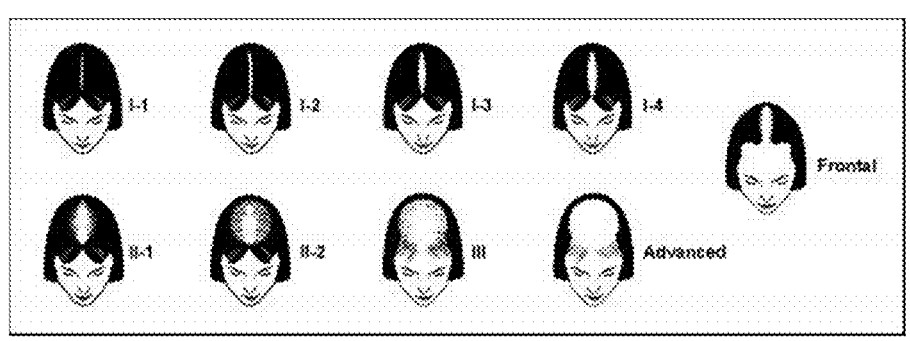
FIG. 2B shows Ludwig scale of female-pattern boldness.

FIG. 2A presents Norwood-Hamilton scale of male-pattern boldness according to "NH Scale," Hairmax Web, available on webpage at hairmax.com/portals/0/NH_scale-.gif. FIG. 2B presents Ludwig scale of female-pattern boldness according to "Ludwig Scale 2," Atlantic Hair Surgeon Web available on atlantahairsurgeon.com/wp-content/uploads/2013/07/ludwig-scale-2.jpg.

Example 1

Methodology and Steps

Patient Information:
Gender: Male
Age: 49
Hair Condition Pre-Treatment: N-H (Norwood-Hamilton) scale 4 (FIG. 2A).
Methodology and Steps:

1. 60 ml of blood including 8 ml of anti-coagulant was collected from the Patient.
2. Thus obtained blood was separated by using HARVEST™ SmartPReP 2 for 14 minutes to obtain 12 ml of plasma, 6 ml of PRP (Platelet Rich Plasma, which may still contain some plasma), and red blood cell (RBC).
3. A sterilized polypropylene container containing plasma was submerged in 100° C. temperature water for 5 minutes to obtain 12 ml of gel-type plasma.
4. 500 μg of the freeze-dried commercial product of bFGF (TRAFERMINTM: KAKEN PHARMACEUTICAL CO., LTD.) was dissolved into 5 ml of saline solution for injection, to prepare a 100 μg/ml of bFGF solution.
5. Prepared the following two agents (a) and (b):
   (a) 12 ml of gel-type plasma+2 ml of prepared bFGF solution+2 ml of compound solution obtained from Step 5(b) below (total amount of solution obtained is 16 ml),
   (b) 6 ml of PRP+3 ml of prepared bFGF solution (the total amount of solution obtained is 9 ml; 2 ml was added to make solution (a), so 7 ml was left).
6. Anesthetic procedure. Specifically, anesthetization of nerve blocks of bilateral Supraorbital Nerve, Supratrochlear Nerve, and Great Occipital Nerve was performed.
7. Target areas were treated with (Auto) Micro-needle Therapy System (MTS).
8. Into the MTS-treated target area, agent (a) gel-type plasma+PRP+bFGF solution and agent (b) PRP+bFGF solution were administered in sequence.
9. The patient was treated 3 times in total, once every 28 days by repeating the same procedure.

Example 2

Clinical Research on Patients and Results

The percentage of hair density was measured with Digital Scope BEAUTOPIA IS5000, being the reference point at temporal area, which is the least influence of hair loss, to compare with a target site.

Case 1)

| Gender: | Male |
|---|---|
| Age: | 52 |

Hair Condition Pre-Treatment: N-H (Norwood-Hamilton) scale 3 vertex type (in FIG. 2B).
Hair density Change: 5%→43% (4 months later after 3 procedures in 3 months) Steps of Procedure:
Step 1—40 ml of blood was drawn from the patient;
Step 2—Thus-obtained blood was separated by centrifuge to get 4 ml of PRP (platelet rich plasma) and 8 ml of plasma;
Step 3—Plasma obtained in step 2 was put into a sterile container and submerged in 100° C. water for 5 minutes to get 8 ml of gel-type plasma;
Step 4—500 μg of the freeze-dried commercial bFGF was dissolved into 5 ml of saline solution to prepare 100 μg/ml of bFGF solution;
Step 5—The following two agents (a) and (b) were prepared:
   (a) gel-type plasma (8 ml)+bFGF solution (1 ml)+prepared solution (b) below (1.5 ml),
   (b) PRP (4 ml)+bFGF solution (2 ml);
Step 6—Anesthetic procedure was conducted on the patient's head;
Step 7—Target area was treated with micro-needle therapy system (MTS);
Step 8—Agents (a) gel-type plasma+PRP+bFGF solution and (b) PRP+bFGF solution in sequence were administered by injection into the MTS-treated area; and
Step 9—The above treatment was repeated 2 times more over a four-month period.
FIG. 3A shows the target area before the first treatment. FIG. 3B shows the target area 4 months after the first treatment.

The subject in Case 1 is an individual with male pattern baldness, Androgenic Alopecia, of N-H (Norwood-Hamilton) scale 3 vertex type. Onset of his hair loss was about 10 years ago. Following the procedure once a month for 4 months, his hair density increased from 5% (FIG. 3A) to 43% (FIG. 3B), respectively, at the target area at the fourth month. When the treatment area was observed 1 month after the first procedure, the subject noticed new hair grow where there previously had been none and darkening of the follicles of old hair. At the fourth month, a substantial amount of new hair growth was on notice and continues to increase in density.

Case 2)

| Gender: | Male |
|---|---|
| Age: | 45 |

Hair Condition Pre-Treatment: N-H (Norwood-Hamilton) scale 4 (in FIG. 2A).
Hair density Change: 5%→49% (56 days after the first procedure)
Steps of Procedure:
Step 1—60 ml of blood was drawn from the patient;
Step 2—Thus-obtained blood was separated by centrifugation to get 6 ml of PRP (platelet rich plasma) and 12 ml of plasma;
Step 3—Thus plasma in Step 2 was put into a sterile container and submerged in 100° C. water for 5 minutes to get 12 ml of gel-type plasma;
Step 4—500 μg of the freeze-dried commercial bFGF was dissolved into 5 ml of saline solution to prepare 100 μg/ml of bFGF solution;
Step 5—The following two agents (a) and (b) were prepared:
   (a) gel-type plasma (12 ml)+bFGF solution (2 ml)+prepared solution (b) below (2 ml),
   (b) PRP (6 ml)+bFGF solution (3 ml);
Step 6—Anesthetic procedure was conducted on the patient's head;
Step 7—Target area of head was treated with micro-needle therapy system (MTS);
Step 8—Agents (a) gel-type plasma+PRP+bFGF solution and (b) PRP+bFGF solution in sequence were administered by injection to the MTS-treated surface; and
Step 9—The above treatment was repeated 1 more time after the first procedure.

Figure 4A:
FIG. 4A shows an illustrative embodiment of a target area before the treatment in accordance with the disclosure in Case 2.
Figure 4B:
FIG. 4B shows an illustrative embodiment of a target area 56 days after the treatment in accordance with the disclosure in Case 2.

FIG. 4A shows the target area before the first treatment. FIG. 4B shows the target area 56 days after the first treatment.

The subject in Case 2 is an individual with androgenic alopecia with hair loss type N-H (Norwood-Hamilton) scale 4. His onset of hair loss started about 5 years ago. Following two procedures, his hair density increased from 5% (FIG. 4A) to 49% (FIG. 4B) at the target area. FIG. 4B was taken on the 56th day from the first procedure and his third procedure will take place.

Case 3)

| Gender: | Female |
|---|---|
| Age: | 44 |

Hair Condition Pre-Treatment: Bilateral temporal hair loss due to previous radiation therapy Hair density Change: 3%→43% (56 days after the first procedure)

Steps of Procedure:

Step 1—Collected 20 ml of blood from the patient;

Step 2—Separated obtained blood by centrifuge to get 2 ml of PRP (platelet rich plasma) and 4 ml of plasma;

Step 3—Obtained plasma was put into a sterile container and submerged in 100° C. water for 5 minutes to get 4 ml of gel-type plasma;

Step 4—Dissolved 500 µg of the freeze-dried commercial bFGF into 5 ml of saline solution to prepare 100 µg/ml of bFGF solution;

Step 5—Prepared the following two Agents (a) and (b):

(a) gel-type plasma (4 ml)+bFGF solution (0.5 ml)+ solution (b) below (0.5 ml), (b) PRP (2 ml)+bFGF solution (2 ml);

Step 6—Conducted anesthetic procedure on the patient's head;

Step 7—Prepared target area by treating it with micro-needle therapy system (MTS);

Step 8—Injected the treated target area with compound (a) gel-type plasma+PRP+bFGF solution and compound (b) PRP+bFGF solution in sequence; and Step 9—Repeated the above treatment 1 more time after the first procedure.

Figure 5A:
FIG. 5A and 5 B show an illustrative embodiment of a target area before the first treatment depicting left and right temporal areas in accordance with the disclosure in Case 3.
Figure 5B:
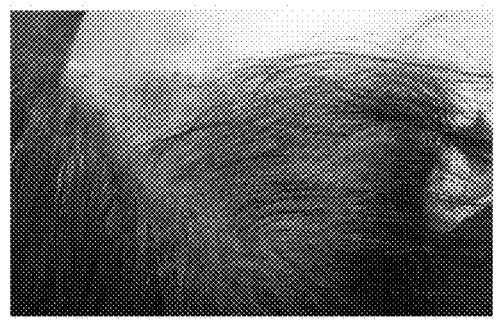
FIG. 5C and 5D show an illustrative embodiment of a target area 56 days after the first treatment in accordance with the disclosure in Case 3.
Figure 5C:
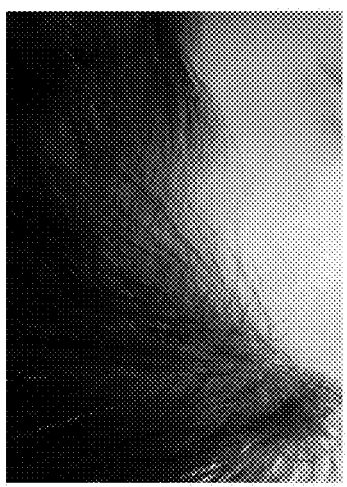
Figure 5D:
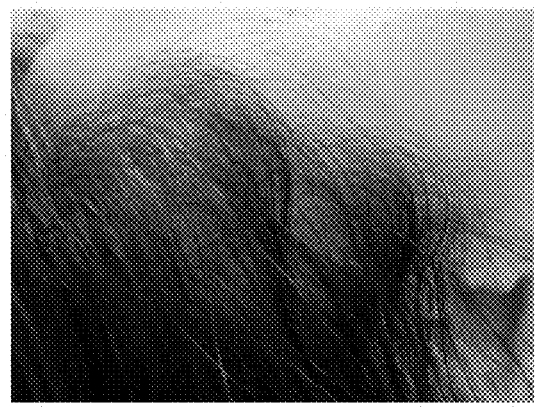

FIGS. 5A and 5B show the target area before the first treatment depicting left and right temporal areas. FIGS. 5C and 5D show the target area 56 days after the first treatment.

The subject in Case 3 is a female individual with a history of radiation therapy at left temporal area due to left temporal lobe brain tumor 5 years ago. Hair loss on the left side of temporal area was more severe than the right side. Following the procedure twice, at 4 weeks interval, her hair density increased from 3% (FIGS. 5A and 5B) to 43% (FIGS. 5C and 5D) at the target area at 56 days.

Case 4)

| Gender: | Male |
|---|---|
| Age: | 67 |

Hair Condition Pre-Treatment: M shaped male baldness with N-H (Norwood-Hamilton) scale 4 (in FIG. 2A).

Hair density Change: 6%→49% (at 3-month point after 3 procedures every 4 weeks).

Steps of Procedure:

Step 1—Collected 60 ml of blood from the patient;

Step 2—Separated obtained blood by centrifuge to get 6 ml of PRP (platelet rich plasma) and 12 ml of plasma;

Step 3—Obtained plasma put into a sterile container and submerged in 100° C. water for 5 minutes to get 82 ml of gel-type plasma;

Step 4—Dissolved 500 µg of the freeze-dried commercial bFGF into 5 ml of saline solution to prepare 100 µg/ml of bFGF solution;

Step 5—Prepared the following two Agents (a) and (b):

(a) gel-type plasma (12 ml)+bFGF solution (2 ml)+ solution (b) below (2 ml), (b) PRP (6m1)+bFGF solution (3 ml);

Step 6—Administered anesthetic procedure on the patient;

Step 7—Prepared target area by treating with micro-needle therapy system (MTS);

Step 8—Injected the MTS-treated target area with Agents (a) gel-type plasma+PRP+bFGF solution and (b) PRP+ bFGF solution in sequence; and Step 9—Repeated the above treatment 2 more time at an interval of 4 weeks.

Figure 6A:
FIG. 6A shows an illustrative embodiment of a target area before the first treatment in accordance with the disclosure in Case 4.
Figure 6B:
FIG. 6B shows an illustrative embodiment of a target area 3 month after the first treatment in accordance with the disclosure in Case 4.

FIG. 6A shows the target area before the first treatment. FIG. 6B shows the target area about 3 month after the first treatment.

The subject in Case 4 is a male individual with hair condition of N-H (Norwood-Hamilton) scale 4. His onset of hair loss started about 25 years ago. Following the procedures once every 4 weeks for 3 months, his hair density increased from 6% (FIG. 6A) to 49% (FIG. 6B) at the target area at the third month. When the treatment area was observed 1 month after the first procedure, the subject noticed new fine hair grow and thickening of hair shaft.

Case 5)

| Gender: | Female |
|---|---|
| Age: | 37 |

Hair Condition Pre-Treatment: Ludwig scale alopecia areata

Hair density Change: 0%→59% (56 days after the first procedure).

Steps of Procedure:

Step 1—Collected 20 ml of blood from the patient;

Step 2—Separated obtained blood by centrifuge to get 2 ml of PRP (platelet rich plasma) and 4 ml of plasma;

Step 3—Obtained plasma put into a sterile container and submerged in of 100° C. water for 5 minutes to get 4 ml of gel-type plasma;

Step 4—Dissolved 500 µg of the freeze-dried commercial bFGF into 5 ml of saline solution to prepare 100 µg/ml of bFGF solution;

Step 5—Prepared the following two Agents (a) and (b):

(a) gel-type plasma (4 ml)+bFGF solution (0.5 ml)+ solution (b) below (0.5 ml), (b) PRP (2 ml)+bFGF solution (2 ml);

Step 6—Performed an anesthetic procedure on the patient's head;

Step 7—Prepared target area by treating with micro-needle therapy system (MTS);

Step 8—Injected the MTS-treated target area with compound (a) gel-type plasma+PRP+bFGF solution and compound (b) PRP+bFGF solution in sequence; and Step 9—Repeated the above treatment one more procedure 4 weeks after the first procedure.

Figure 7A:
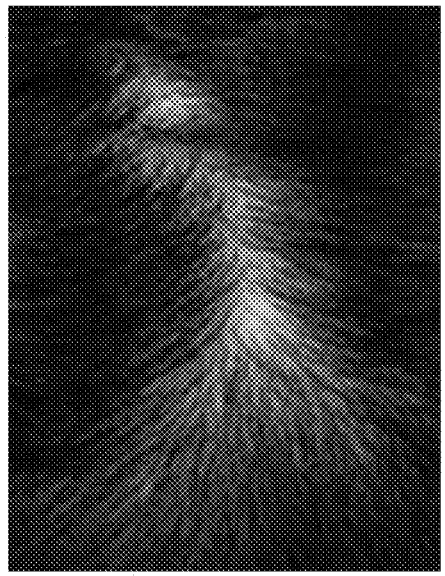
FIG. 7A shows an illustrative embodiment of a target area before the first treatment in accordance with the disclosure in Case 5.
Figure 7B:
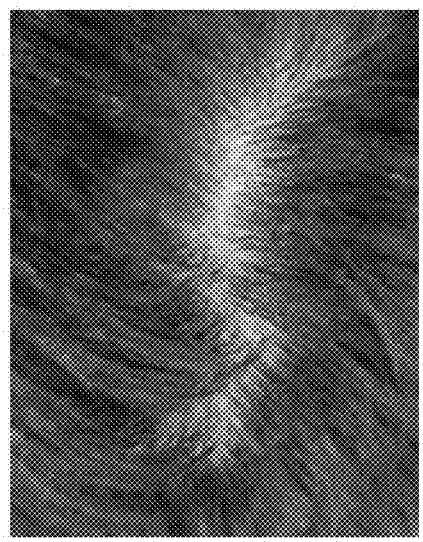
FIG. 7B shows an illustrative embodiment of a target area 2 months after the first treatment in accordance with the disclosure in Case 5.

FIG. 7A shows the target area before the first treatment. FIG. 7B shows the target area 56 days after the first treatment.

The subject in Case 5 is a female individual with Alopecia Areata with Ludwig scale I-3. Her onset of hair loss started about a year ago. Following the procedure, 2 procedures in 4 weeks interval, her hair density increased from 0% (FIG. 7A) to 59% (FIG. 7B) at the target area at 56 days after the first procedure.

TABLE

| Cases | Sex | Age | Sclae | Number of Procedures | Hair Density start | Hair Density post treatment |
|---|---|---|---|---|---|---|
| Case 1 | M | 52 | Androgenic Aloprcia 3 vertex | 3 | 5% | 43% |
| Case 2 | M | 45 | Androgenic Alopecia 4 | 2 | 5% | 49% |
| Case 3 | M | 44 | Radiation therapy hair loss 3A | 2 | 3% | 43% |
| Case 4 | M | 67 | Androgenic Alopecia 4 | 3 | 6% | 49% |
| Case 5 | F | 37 | Alopecia Areata | 2 | 0% | 59% |

Figure 8A:
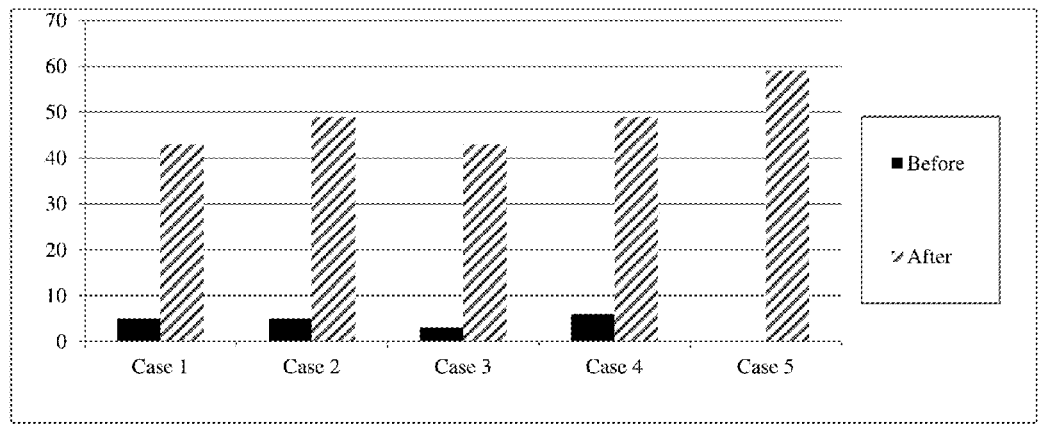
FIG. 8A shows a chart comparing hair density before and after the treatment in accordance with the disclosure in Cases 1-5.
Figure 8B:
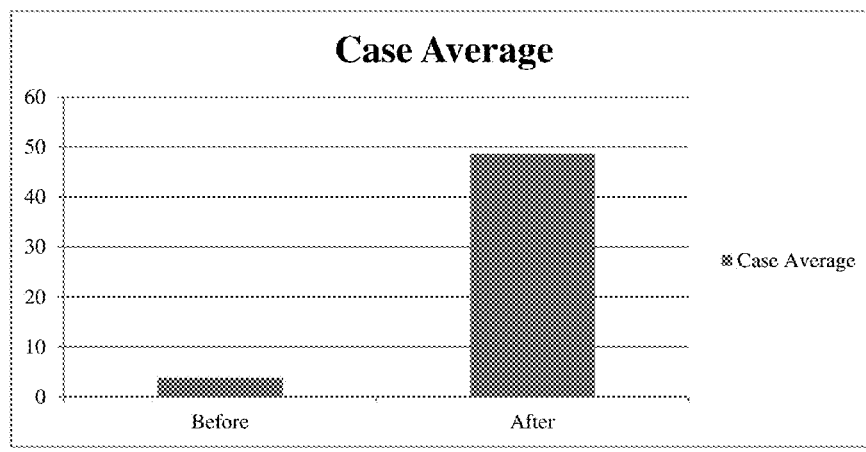
FIG. 8B shows a chart showing a hair growth average in accordance with the disclosure in Cases 1-5.

FIG. 8A is a chart comparing hair density before and after the treatment in Case Examples 1-5. FIG. 8B is a chart showing a hair growth average in Case Examples 1-5.

These 5 Cases on average demonstrated that the subject's average of hair density was less than 5% before the procedures. The average hair density of the 5 Cases increased over 45% following 1 to 3 procedures, depending on the condition of hair loss.

INDUSTRIAL APPLICABILITY

The application of the Agent can promote or stimulate significant hair growth and prevent unwanted hair loss in individuals.

While the various embodiments above contain different procedures and features, upon reading the specification, one skilled in the art readily will realize that such procedures and features in one embodiment may be incorporated into or combined with procedures and features of another embodiment. Also, the previous description of the embodiments is provided to enable a person skilled in the art to make and use the present disclosure. Moreover, various modifications to these embodiments will be readily apparent to those skilled in the art, and the generic principles and specific examples defined herein may be applied to other embodiments without the use of inventive faculty. Therefore, the present disclosure is not intended to be limited to the embodiments described herein but is to be accorded the widest scope as defined by the limitations of the claims and equivalents thereof.

What is claimed is:

1. A composition comprising, as active ingredients in amounts effective to promote hair growth of a subject:
   (a) basic fibroblast growth factor (bFGF);
   (b) platelet rich plasma (PRP), and
   (c) blood plasma,
   wherein the blood plasma is in a gel-like form, which is obtained by placing a container containing blood plasma in water at a temperature of 0-100° C. for up to 10 minutes, and
   wherein a volume ratio of said (a) : (b) : (c) is about 1 : 1.09 : 2.36.

2. The composition of claim 1, wherein the subject has a hair loss disorder selected from the group consisting of alopecia greata, androgenic alopecia, alopecia areata, alopecia universalis, involutional alopecia, trichotillomania, telogen effluvium, anagen effluvium, cicatricial, alopecia, scarring alopecia, scalp thinning, hair shaft abnormalities, infectious hair disorders, genetic disorders, hair loss due to chemotherapy, hormonal imbalance, fungal infection, medication intake, and chemical hair treatment.

3. The composition of claim 1, wherein the subject is suffering from hair loss, said hair loss being associated with at least one disease selected from the group consisting of diabetes, lupus, poor nutrition, mental stress, and physical stress.

4. The composition of claim 1, which further comprises a pharmaceutically acceptable carrier.

5. The composition of claim 1, which is injectable.

6. A composition comprising, as active ingredients in amounts effective to promote hair growth of a subject:
   (a) basic fibroblast growth factor (bFGF);
   (b) platelet rich plasma (PRP), and
   (c) blood plasma,
   wherein the blood plasma is in a gel-like form, which is obtained by placing a container containing blood plasma in water at a temperature of 0-100° C. for up to 10 minutes, and
   wherein a volume ratio of said (a) : (b) : (c) is about 1 : 0.8-1.3 : 1.6-2.7.

7. The composition of claim 6, wherein the subject has a hair loss disorder selected from the group consisting of alopecia greata, androgenic alopecia, alopecia areata, alopecia universalis, involutional alopecia, trichotillomania, telogen effluvium, anagen effluvium, cicatricial, alopecia, scarring alopecia, scalp thinning, hair shaft abnormalities, infectious hair disorders, genetic disorders, hair loss due to chemotherapy, hormonal imbalance, fungal infection, medication intake, and chemical hair treatment.

8. The composition of claim 6, wherein the subject is suffering from hair loss, said hair loss being associated with at least one disease selected from the group consisting of diabetes, lupus, poor nutrition, mental stress, and physical stress.

9. The composition of claim 6, which further comprises a pharmaceutically acceptable carrier.

10. The composition of claim 6, which is injectable.

11. A kit comprising
   a first container comprising a blood plasma, platelet rich plasma (PRP), and basic fibroblast growth factor (bFGF), and
   a second container containing a blood plasma and a bFGF,
   wherein the blood plasma is in a gel-like form, which is obtained by placing a container containing blood plasma in water at a temperature of 0-100° C. for up to 10 minutes;
   wherein each of the total amounts of the gel-type form blood plasma, PRP, and bFGF is an amount effective to promote hair growth of a subject suffering from hair loss; and
   wherein a total volume ratio of bFGF : PRP : gel-like form blood plasma is about 1 : 0.8-1.3 : 1.6-2.7.

* * * * *